US009580525B2

(12) United States Patent
Mathys et al.

(10) Patent No.: US 9,580,525 B2
(45) Date of Patent: Feb. 28, 2017

(54) OLEFIN OLEGOMERIZATION PROCESS

(71) Applicant: ExxonMobil Chemical Patents Inc., Baytown, TX (US)

(72) Inventors: Georges M. K. Mathys, Bierbeek (BE); Geraldine Tosin, Notre Dame de Gravenchon (FR); Johan A. Martens, Huldenberg (BE); Marcel J. G. Janssen, Kessel-Lo (BE); Joris Franken, Genk (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 360 days.

(21) Appl. No.: 14/348,369

(22) PCT Filed: Sep. 18, 2012

(86) PCT No.: PCT/EP2012/068297
§ 371 (c)(1),
(2) Date: Mar. 28, 2014

(87) PCT Pub. No.: WO2013/064302
PCT Pub. Date: May 10, 2013

(65) Prior Publication Data
US 2014/0256892 A1 Sep. 11, 2014

(30) Foreign Application Priority Data
Oct. 31, 2011 (EP) .................................... 11187214

(51) Int. Cl.
*C08F 110/08* (2006.01)
*C07C 2/12* (2006.01)

(52) U.S. Cl.
CPC ............... *C08F 110/08* (2013.01); *C07C 2/12* (2013.01); *C07C 2529/14* (2013.01)

(58) Field of Classification Search
CPC .................................. C08F 110/08; C07C 2/12
See application file for complete search history.

(56) References Cited

U.S. PATENT DOCUMENTS

| 3,325,465 A | 6/1967 | Jones et al. |
| 4,517,399 A | 5/1985 | Chester et al. |

(Continued)

FOREIGN PATENT DOCUMENTS

| EP | 0 261 730 | 3/1988 |
| EP | 0 625 132 | 11/1994 |

(Continued)

OTHER PUBLICATIONS

Denayer, J.F.M. et al., "*Removal of cyclopentadiene from 1-octene by transition metal containing zeolites—Part 2: Stabilization of CoCaX zeolite by its cation distribution*" Microporous and Mesoporous Materials, 103 (2007) pp. 11-19.
Gonzalez. G. et al., "*New zeolite topologies based on intergrowths of FAU/EMT systems*", Microporous and Mesoporous Materials, Elsevier, vol. 101, Nos. 1-2, (2007) pp. 30-42.

(Continued)

*Primary Examiner* — Catherine S Branch
(74) *Attorney, Agent, or Firm* — Darryl M. Tyus

(57) ABSTRACT

An olefin oligomerization process comprises contacting an olefin feed with a catalyst composition. The catalyst composition includes a crystalline aluminosilicate having FAU, EMT or a combination of FAU and EMT framework type. The crystalline aluminosilicate has cobalt and at least one alkaline earth metal selected from calcium, barium, strontium and mixtures thereof within its intra-crystalline cages.

14 Claims, 5 Drawing Sheets

(56) References Cited

U.S. PATENT DOCUMENTS

| | | | |
|---|---|---|---|
| 5,108,970 | A | 4/1992 | Young et al. |
| 5,552,357 | A | 9/1996 | Lago et al. |
| 5,571,768 | A | 11/1996 | Chang et al. |
| 5,610,112 | A | 3/1997 | Lago et al. |
| 5,612,270 | A | 3/1997 | Beck et al. |
| 5,625,104 | A | 4/1997 | Beck et al. |
| 2004/0068072 | A1 | 4/2004 | Small |
| 2011/0172482 | A1* | 7/2011 | Cabiac ............... B01J 29/041 585/502 |

FOREIGN PATENT DOCUMENTS

| | | |
|---|---|---|
| GB | 1095982 | 12/1967 |
| GB | 1124765 | 8/1968 |
| GB | 1124766 | 8/1968 |
| GB | 1183201 | 3/1970 |
| WO | 95/22516 | 8/1995 |
| WO | 03/082780 | 10/2003 |

OTHER PUBLICATIONS

Martens J. A. et al., "*Tailored Alkene Oligomerization with H-ZSM-57 Zeolite*", Angew. Chem. Int. Ed. (2000) 39, pp. 4376-4379.

Martens J. A. et al., "*Tailored Catalytic Propene Trimerization over Acidic Zeolites with Tubular Pores*", Angewandte Chemie International Edition (2005) 44, pp. 5687-5690.

Nkosi, B. et al., "*The oligomerization of butenes with partially alkali exchanged NiNa Y zeolite catalysts*" Applied Catalysis A: General, vol. 158, No. 1-2 (1997) pp. 225-241.

Schultz et al., "*Olefin Dimerization over Cobalt-Oxide-On-Carbon Catalysts I. Propylene Dimerization*", Journal of Catalysis 6 (1966) pp. 385-396.

Schultz, R.G. et al., "*Olefin Dimerization over Cobalt-Oxide-on-Carbon Catalysts II. Butene and Hexene Dimerization*", Journal of Catalysis 6 (1966) pp. 419-424.

Hassan, S.M. et al., "Studies on the Mechanism and Kinetics of Propylene Oligomerization and Hydrooligomerization on Zeolites", Bulletin of the Chemical Society of Japan, vol. 50 (10), (1977) pp. 2597-2601.

\* cited by examiner

OLEFIN OLEGOMERIZATION PROCESS

PRIORITY CLAIM TO RELATED APPLICATIONS

This application is a National Stage Application of International Application No. PCT/EP2012/068297 filed Sep. 18, 2012, which claims priority to European Application No. 11187214.9 filed Oct. 31, 2011, the disclosures of which are fully incorporated herein by their reference.

FIELD OF THE INVENTION

The present invention relates to an olefin oligomerization process, a catalyst composition, a method for producing the catalyst composition and the use of such catalyst composition in olefin oligomerization.

BACKGROUND OF THE INVENTION

Propene and butene oligomerization into C6 to C16 olefins (also referred to as higher olefins) are industrially important petrochemical processes. These higher olefins are used for example as intermediates in hydroformylation processes leading to valuable chemicals. The branching degree of the higher olefin and the position of the carbon-carbon double bond determine the reactivity in hydroformylation. Most valuable are linear and little branched oligomers. Olefins with low or medium branching index and alpha-olefins in particular find application in plasticizer and surfactant synthesis. Strongly branched oligomers are less desired but can be added to the gasoline pool.

Solid phosphoric acid (SPA) has been widely used as a catalyst for oligomerization of feedstreams containing alkenes with 2 to 12 carbon atoms. However, SPA produces significant amounts of undesired cracked products, it cannot be regenerated and has to be disposed of at the end of the operation or when its activity is no longer satisfactory. Homogeneous catalysts, especially nickel complexes, are known to yield quasi linear oligomers. An example of a homogeneous process is the Difasol process. Homogeneous catalysts, however, present a problem of catalyst recovery. Heterogeneous nickel catalysts are also used for olefin oligomerization such as in the Octol processes. Nickel catalysts are also sensitive to feed impurities such as sulphur and nitrogen components.

Various zeolites have been proposed as an alternative to SPA or to nickel containing species as oligomerization catalysts. For example, U.S. Pat. No. 4,517,399 reports an olefin oligomerization process in which a feedstock containing olefins is passed over a ZSM-5 zeolite catalyst. U.S. Pat. No. 5,571,768, U.S. Pat. No. 5,612,270, U.S. Pat. No. 5,552,357, U.S. Pat. No. 5,625,104 and U.S. Pat. No. 5,610,112 indicate the use of selectivated forms of ZSM-5 and of other zeolites having a constraint index from 1 to 12, namely, ZSM-11, ZSM-12, ZSM-22, ZSM-23, ZSM-35, ZSM-48, ZSM-50 and ZSM-57 in olefin oligomerization. WO 93/16020 discloses an alkene oligomerization process over a zeolite catalyst selected from zeolites of the TON(H-ZSM-22, H-ISI-1, H-Theta-1 H-Nu-10, KZ-2), MTT (H-ZSM-23, KZ-1), MFI (H-ZSM-5), MEL (HZSM-11), MTW (H-ZSM-12) or EUO (EU-1) structure types, H-ZSM57, zeolites of the ferrierite structure family, offretites, H-ZSM-4, H-ZSM-18, zeolite Beta, faujasites, zeolite L, mordenites, errionites and chabazites.

WO 95/22516 discloses an olefin oligomerization process with improved selectivity to certain oligomers. The process is carried out over a catalyst comprising at least one molecular sieve having a refined constraint index greater than 10 and at least one molecular sieve having a refined constraint index within the range of from 2 to 10. Examples of molecular sieves having a refined constraint index greater than 10 include ZSM-22, ZSM-23 and certain ferrierites. Examples of molecular sieves having a constraint index within the range of from 2 to 10 include ZSM-5, 11, 12, 35, 38, 48 and 57, SAPO-11, MCM-22 and erionite.

Heterogeneous acid catalysts such as supported phosphoric acid or zeolites mainly result in branched oligomers. In Angewandte Chemie International Edition 2000, 30, 4376-4379, J. A. Martens and R. Ravishankar reported a process for dimerization of butene over ZSM-57, achieving a conversion level of 89% and a dimer product selectivity of 85.7%. The octene (dimer) fraction mainly comprised dimethylhexenes (76% of the octene fraction). The branching index of the dimer fraction therefore approached a value of 2. In Angewandte Chemie International Edition 2005, 44, 5687-5690, J. A. Martens and W. H. Verrelst reported a study on propene oligomerization over ZSM-22, in which ZSM-22 showed very high propene conversion with high yields of dimer and trimer products. The dimer fraction consisted mainly of methylbranched hexenes, with a significant amount of linear hexenes. Within the trimer fraction, dibranched nonenes were dominant products. When the outer catalyst surface was poisoned with collidine, ZSM-22 even gave a trimer fraction extremely rich in monobranched products (80%) with a significant amount of linear trimers (15%).

There remains a need for alternative oligomerization processes with high conversion, product selectivity and which provide oligomers of high linearity. There further exists a need for alternative catalysts to conventional zeolite, SPA and nickel catalysts that can achieve high conversion, product selectivity and product linearity in oligomerization processes.

WO 03/082780 discloses selectivated ZSM-22 or ZSM-23 molecular sieves as oligomerization catalysts to provide products such as octenes and dodecenes from butene, having low degree of branching and a low amount of hindered double bonds. Oligomerization is preferably carried out at a temperature from 190 to 230° C.

US20040068072 discloses cobalt containing organometallic catalysts for dimerization of olefins. Oligomerization is preferably carried out in the temperature range of 10 to 50° C.

GB1124765, GB1124766, GB1183201, GB1095982, Journal of Catalysis 6, 385-396 and 419-424, Robert Schultz et al. (1966), all teach cobalt containing activated carbon catalysts for oligomerization of olefins. The preferred process temperature ranges from −20 to 90° C.

In Bulletin of Chem. Soc. Jap p. 2597-2601 (1997), Kuznetsov et al. disclose the use of modified FAU type zeolite catalysts. On CoY, CaY, CoX hydrooligomerization takes place. The most preferred catalyst, NiX, is used for selective oligomerization of propylene. CoY is obtained by direct ion exchange of NaY to CoNaY. At about 85% NaY exchange the product was $Co_{3.5}Na_1Al_8Si_{184}O_{384}$. CoX was obtained by direct exchange of NaX to CoNaX. At about 65% NaX exchange the product was $Co_{28}Na_{31}Al_{87}Si_{105}O_{384}$. Oligomerization was carried at out a temperature of at least 190° C.

EP 261730 discloses a method for the dimerization of olefins, in particular olefins having between 4 and 24, and preferably between 10 and 20 carbon atoms, using zeolite X and Y having alkaline metals on 10 to 50% of its exchangeable sites, a bivalent or trivalent metal on 1-30% of its exchangeable sites, and the remainder of the exchangeable sites being acid sites.

Microporous and Mesoporous Materials 103 (2007) p. 1-19, J. Denayer et al. describes the use of zeolite X containing cobalt and calcium for removal of cyclopentadiene from 1-octene. CoCaX is made by exchanging NaX to NaCaX, followed by calcination. The obtained NaCaX is then exchanged to CoCaX. The product is $Co_{34}Ca_9Al_{86}Si_{106}O_{384}$.

SUMMARY OF THE INVENTION

The present invention provides an olefin oligomerization process comprising contacting an olefin feed with a catalyst composition under conditions suitable for oligomerization, wherein the catalyst composition comprises a crystalline aluminosilicate molecular sieve having the FAU, the EMT or a combination of FAU and EMT framework types, the molecular sieve having cobalt and at least one alkaline earth metal selected from calcium, barium, strontium and mixtures thereof within its intra-crystalline cages.

Preferably the crystalline aluminosilicate of the FAU, the EMT or a combination of the FAU and EMT framework types suitable for use in this process has a composition according to formula (I):

$$Co_xM1_yM2_zAl_pSi_{192-p}O_{384} \qquad (I)$$

wherein:
p is the number of aluminium atoms per mol of aluminosilicate, and p is at least 40 but is not greater than 96;
x is the number of Co atoms per mol of aluminosilicate and x is at least 4, but is not greater than (p/2)−5;
M1 is calcium, barium, strontium or a mixture thereof, preferably calcium;
y is the number of M1 atoms per mol of aluminosilicate, and y is at least 5, but is not greater than (p/2)−x;
M2 is sodium, potassium or a mixture thereof, preferably sodium;
z is the number of M2 atoms per mol of aluminosilicate, and z≥0 and z=p−2x−2y.

In a preferred embodiment, the crystalline aluminosilicate is of formula (I), in which p is at least 50, but is not greater than 76, x is at least 4 and is not greater than 10, y is at least 10 and is not greater than 16 and z>0 and z=p−2x−2y.

Preferably the olefin feed comprises C3 to C6 olefins and most preferred is butene.

The present invention also provides process for the manufacture of the catalyst composition, wherein the process comprises:
a) providing a crystalline aluminosilicate having the FAU, the EMT or a combination of FAU and EMT framework type and having a composition as defined by the following formula (II):

$$M2_pAl_pSi_{192-p}O_{384} \qquad (II)$$

in which: M2 and p have the same meaning as in formula (I);
b) treating the crystalline aluminosilicate of formula (II) with a solution containing a source of M1 ions, in which M1 has the same meaning as in formula (I), in order to form crystalline aluminosilicate having a composition defined by the formula (III):

$$M1_yM2_{z'}Al_pSi_{192-p}O_{384} \qquad (III)$$

in which:
M1, M2, p and y have the same meaning as in formula (I); and z' is the number of M2 atoms per mol of aluminosilicate and z'>0 with z'=p−2q;
c) submitting the product obtained from step b) to a temperature of greater than 300° C.
d) treating the product obtained from step c) with a solution containing a source of cobalt ions, in order to form the crystalline aluminosilicate of formula I.

DETAILED DESCRIPTION OF THE INVENTION

Olefin Feed

Figure 1:
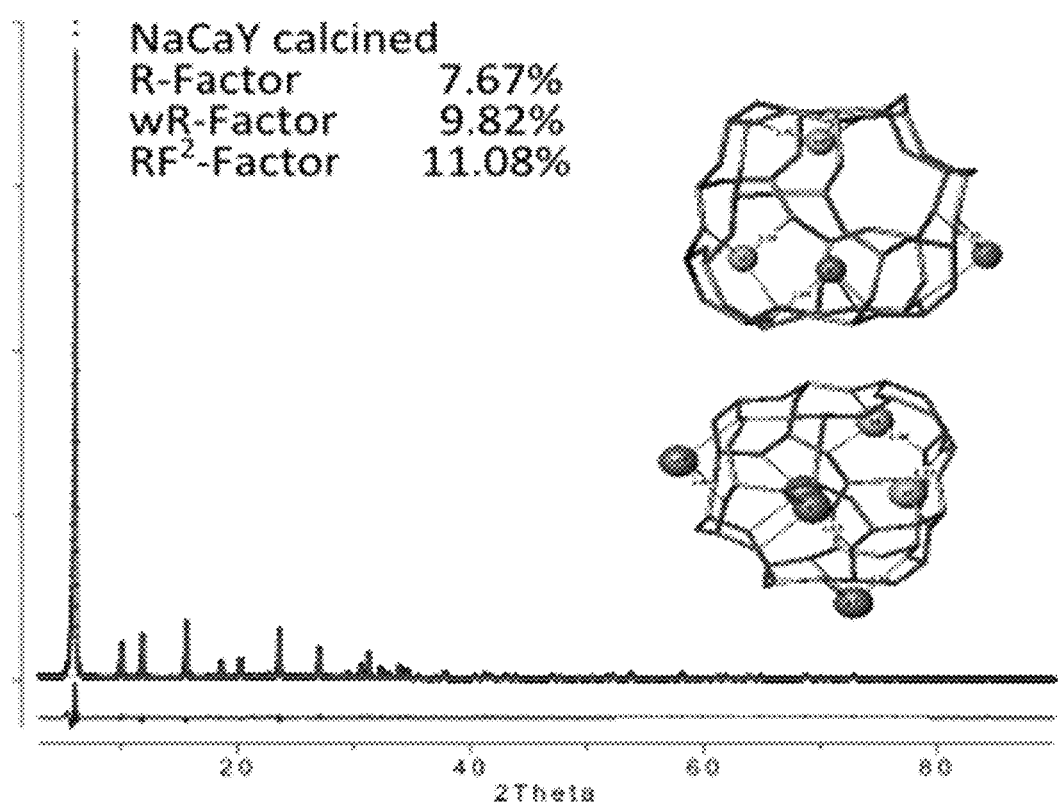
FIG. 1: XRD pattern of calcined NaCaY prepared in example 1.

The present invention provides a process for oligomerizing an olefin feed. As used herein, "olefin" refers to any unsaturated hydrocarbon having the formula $C_nH_{2n}$, including isomers thereof. According to this invention, the olefins in the feed typically have from 2 to 15 carbon atoms, such as at least 3 and no more than 8 carbon atoms, and typically at least 3 and no more than 6 carbon atoms. The olefins present in the feed may also be referred to as lower olefins or light olefins.

The feed may also comprise one or more paraffins. As used herein, "paraffins" refers to any of the saturated hydrocarbons having the formula $C_nH_{2n+2}$. The paraffins that may be present in the olefin feed typically have from 1 to 25 carbon atoms, such as from 1 to 15 carbon atoms, and conveniently at least 3 and no more than 6 carbon atoms. Examples of suitable paraffins include methane, ethane, propane, butane, pentane, hexane, isomers thereof and mixtures thereof.

In a class of embodiments, the olefin feed comprises olefins selected from propene, butenes, pentenes, hexenes, their isomers, and mixtures thereof. The process of this invention is especially useful for the oligomerization of feeds comprising propene, butenes, pentenes, their isomers, and mixtures thereof. As used herein, "isomers" refers to compounds having the same molecular formula but different structural formula.

Examples of suitable olefin feeds include untreated refinery streams such as Fluidized Catalytic Cracking (FCC) streams, coker streams, pyrolysis gasoline streams or reformates.

Other examples of suitable olefin feeds include refinery feeds often referred to as Raffinate-1 (RAF-1), Raffinate-2 (RAF-2) or Raffinate-3 (RAF-3). Typically, Raffinate-1, Raffinate-2 and Raffinate-3 may be regarded as streams obtainable at various stages in the processing of crude $C_4$ streams obtained from petroleum refining processes. These streams are usually from olefin steam crackers but may also come from refinery catalytic crackers, in which case they generally contain the same components but in different proportions. The first stage of processing these crude $C_4$ refinery streams is to remove butadiene from these streams, such as by solvent extraction or hydrogenation. Butadiene is generally present in the crude $C_4$ refinery streams as 40-45 wt. % of the stream. The product obtained after butadiene removal is Raffinate-1. It generally consists of isobutylene, the two isomers of n-butene, 1-butene and 2-butene, and smaller quantities of butanes and other compounds. The next step consists in removing isobutylene, usually by reaction of isobutylene with methanol to produce methyl-tert-butylether (MTBE), which then produces Raffinate-2. Raffinate-3 (RAF-3) is less common but may be obtained after separation of 1-butene from Raffinate-2. Raffinate-3 typically has a residual 1-butene content of about 1%.

In another embodiment, the feed comprises an FCC light olefin stream that typically comprises ethane, ethylene, propane, propylene, isobutane, n-butane, butenes, pentanes, and other optional components.

In a further class of embodiments, "oligomer(s)" refers to an olefin (or a mixture of olefins) having 20 carbon atoms or less, alternatively, 15 carbon atoms or less, such as 10 carbon atoms or less, alternatively, 9 carbon atoms or less, and conveniently, 8 carbon atoms or less that has been obtained by linking two or more light olefins together. As used herein, "oligomerization process" refers to any process by which light olefins are linked together to form the oligomer(s) as defined above.

In a class of embodiments, the feed comprises between 0.1 wt % and 20 wt % olefins, based upon the total weight of the olefin feed. Alternatively, the feed comprises up to 30 wt % or more olefins, such as 40 wt % or more olefins, alternatively, 50 wt % or more olefins, alternatively, 60 wt % or more olefins, alternatively, 70 wt % or more olefins, and alternatively, 80 wt % or more olefins, based upon the total weight of the olefin feed.

Catalyst Composition

The present invention provides an oligomerization process comprising contacting the olefin feed with an oligomerization catalyst which comprises a crystalline aluminosilicate having the FAU, the EMT or a combination of FAU and EMT framework type, said crystalline aluminosilicate having cobalt and at least one alkaline earth metal selected from calcium, barium, strontium and mixtures thereof within its intra-crystalline cages.

Aluminosilicates are a well-known class of molecular sieve materials which have found widespread use as catalysts and absorbents. The basic structure of these crystalline materials comprises $SiO_4$ tetrahedra (which have four oxygen atoms at the apexes with the silicon atom being at the center) and $AlO_4$ tetrahedra (which have four oxygen atoms at the apexes with the aluminum atom being at the center). These tetrahedra are regularly and three dimensionally connected to each other throughout the structure through the sharing of apex oxygen atoms. This arrangement provides a three-dimensional network structure defining pores that differ in size and shape depending on the arrangement of tetrahedra and composition of the structure. In its simplest terms the material may be considered to be a silicate material in which some of the $Si^{4+}$ ions in the silicate are replaced by $Al^{3+}$ ions. For each $Si^{4+}$ ion replaced by an $Al^{3+}$, the charge must be balanced by having other positive ions such as $Na^+$, $K^+$, or $Ca^{2+}$ present.

As used herein, the expression "framework type" is used with reference to the "Atlas of Zeolite Framework Types", Ch. Baerlocher, L. B. McCusker, D. H. Olson, Sixth Revised Edition, Elsevier 2007. The FAU framework type is assigned to zeolites that have the same crystal framework structure as naturally occurring faujasite. The FAU framework type consists of truncated octahedral (beta cages or sodalite cages) in a tetrahedral arrangement, interconnected through six membered rings (6Rs) to form double six rings (D6Rs or hexagonal prisms), thus forming large intra-crystalline cages (supercages or alpha cages). This way two entwined cage systems are obtained, a small one composed of sodalite cages and a large cavity system made up of intra-crystalline supercages. The small cage system, accessible by the 6Rs only, cannot be penetrated by molecules larger than water or ammonia, though most inorganic cations, the alkali, alkaline earth, and transition metals up to the fourth period can freely enter sodalite cages from the supercages, via a dehydration-surface diffusion phenomenon. D6Rs are only accessible through the 6Rs of the sodalite cages. Examples of crystalline aluminosilicates having the FAU framework type include faujasite, zeolite X (also referred to as Linde X), zeolite Y (also referred to as Linde Y).

Zeolites of FAU framework type are formed of sheets or layers that can stack in different orientations relative to one another. In FAU, the sodalite cages are stacked in an ABCABC sequence where A, B and C refer to three different ways in which the sheets or layers of sodalite cages are stacking one on top of another. These layers are related by a center of inversion in the double 6-member rings. Each layer is shifted laterally before connecting to the previous one. However, upon stacking of the elementary sheets of sodalite cages in an ABAB sequence, with a mirror plane relation between neighbouring layers, a structure with hexagonal rather than cubic symmetry is formed, which corresponds to the EMT framework type. If random stacking of A, B and C layers occurs, a crystal containing intergrown FAU and EMT framework types is obtained. CSZ-1, CSZ-3, ZSM-2, ZSM-3, ZSM-20, ECR-30, ECR-35 and EMC-2 are code names for materials identified as such structural FAU-EMT composites.

As used herein, the expression "crystalline aluminosilicate having the FAU, the EMT or a combination of the FAU and EMT framework-type" thus refers to crystalline aluminosilicates having either a pure cubic FAU structure or a pure hexagonal EMT structure, but also to materials containing intergrown FAU and EMT framework types, which have structures intermediate between a pure FAU framework type and a pure EMT framework type. Further description of the FAU/EMT intergrowth structure may be found in "Collection of Simulated XRD Powder Patterns for Zeolites", M. M. J. Treacy and J. B. Higgins, Fifth Revised Edition, Elsevier, 2007.

Preferably, the crystalline aluminosilicate has the FAU framework type, and more preferably, the crystalline aluminosilicate is zeolite Y.

Preferably the crystalline aluminosilicate of the FAU, the EMT or a combination of the FAU and EMT framework types suitable for use in this process has a composition according to formula (I):

$$Co_xM1_yM2_zAl_pSi_{192-p}O_{384} \qquad (I)$$

wherein:
p is the number of aluminium atoms per mol of aluminosilicate, and p is at least 40 but is not greater than 96;
x is the number of Co atoms per mol of aluminosilicate and x is at least 4, but is not greater than (p/2)−5;
M1 is calcium, barium, strontium or a mixture thereof, preferably calcium;
y is the number of M1 atoms per mol of aluminosilicate, and y is at least 5, but is not greater than (p/2)−x;
M2 is sodium, potassium or a mixture thereof, preferably sodium;

z is the number of M2 atoms per mol aluminosilicate, and z≥0 and z=p−2x−2y.

In a preferred embodiment, the crystalline aluminosilicate is of formula (I), in which p is at least 50, but is not greater than 76, x is at least 4 and is not greater than 10, y is at least 10 and is not greater than 16 and z>0 and z=p−2x−2y.

The catalyst composition of the present invention can be manufactured by wherein the process comprises:
a) providing a crystalline aluminosilicate having the FAU, the EMT or a combination of FAU and EMT framework type and having a composition as defined by the following formula (II):

$$M2_p Al_p Si_{192-p} O_{384} \qquad (II)$$

in which: M2 and p have the same meaning as in formula (I);
b) treating the crystalline aluminosilicate of formula (II) with a solution containing a source of M1 ions, in which M1 has the same meaning as in formula (I), in order to form crystalline aluminosilicate having a composition defined by the formula (III):

$$M1_{y'} M2_{z'} Al_p Si_{192-p} O_{384} \qquad (III)$$

in which:
M1, M2 and p have the same meaning as in formula (I);
y' is the atomic ratio of M1, and it is at least 5, preferably, at least 10;
z' is the number of M2 atoms per mol aluminosilicate and z'>0 with z'=p−2y';
c) submitting the product obtained from step b) to a temperature of greater than 300° C.
d) treating the product obtained from step c) with a solution containing a source of cobalt ions, in order to form the crystalline aluminosilicate of formula I.

With respect to step (a), various crystalline aluminosilicate having the FAU, the EMT or a combination of FAU and EMT framework type are available commercially or may be synthesized by methods well known in the art, such as those described in "Studies in Surface Science and Catalysis" 137 (2001), Introduction to Zeolite Science and Practice, 2nd completely revised and expanded edition, p. 76-78 and p. 138-141. Intergrown FAU and EMT framework types can be synthesized as described in "New Zeolite Topologies Based on Intergrowths of FAU/EMT systems" Microporous and Mesoporous materials 101 (2007) 30-42, Gonzalez et al. Other sources of intergrowth synthesis include "Synthesis and Characterization of Zeolite ZSM-20" D. E. W. Vaughan, M. M. J. Treacy, J. M. Newsam, K. G. Strohmaier, and W. J. Mortier, which appears in "In Zeolite Synthesis" Occelli, M., et al.; ACS Symposium Series; American Chemical Society, Washington D.C., Chapter 37 (1989).

Typically, the manufacture of these crystalline aluminosilicates takes place by forming an aqueous reaction mixture, comprising a source of alumina, a source of silica, and a source of alkali hydroxide, optionally in the presence of an organic structure directing agent, and crystallizing the crystalline molecular sieve at a temperature above room temperature and below 300° C., for a period of time varying from several hours to several days, usually in a pressurized reaction vessel. This produces a crystalline aluminosilicate in which charges created in the zeolite framework are balanced by alkali metal ions.

In step b), the crystalline aluminosilicate of formula (II) is treated with a solution containing a source of M1 ions, in which M1 is selected from calcium, barium, strontium or a mixture thereof. Solutions of calcium, barium or strontium salts are convenient for this purpose. The solvents used to dissolve the salts may be organic or inorganic, the only requirement being that the salt(s) be soluble in the particular solvent. Hydroxylic solvents are preferred, in particular water. Organic solvents may be useful for metal salts which have organic ionic components such as carboxylates, sulphonates, alkoxides, etc. The preferred solutions are aqueous solutions of readily water soluble salts, such as bicarbonates, carbonates, chlorated, perchlorates, hypochlorites, nitrates, nitrites, sulphates, hydrogen sulphates, sulphates, iodatates, halides, and the like.

Treatment with the solution containing the source of M1 ions is performed under conditions that allow control of the amount of M1 ions incorporated into the zeolite framework. It is important to adjust this amount, so some of the M2 ions remain in the zeolite framework after this impregnation step (z' greater than 0). Any conventional impregnation method known to those skilled in the art may be used for this purpose. For example, the zeolite can be dipped in a large volume of solution, which is in excess of the pore volume of the zeolite, removed and shaken of excess liquid. Alternatively, an amount of impregnating liquid considerably less than the pore volume can be sprayed onto an agitated bed of zeolite.

Alternatively, the volume of impregnating liquid can range from about the pore volume to about four of five times, preferably about twice the pore volume of the zeolite to be impregnated. In yet another alternative, a dry impregnation technique can be used, in which just that amount of impregnating solution is used, which will just fill the pores of the zeolite. In other embodiments, baskets of zeolite are dipped into a vat of impregnating solution, removed and dried. Alternatively, the zeolite may be tumbled with the impregnating solution.

The product obtained in step (b) is then heated to a temperature of greater than 300° C. This thermal treatment may take place in the presence of air, or in an atmosphere enriched in nitrogen. Preferably, air is used during this thermal treatment. Preferably the temperature should not be greater than 550° C. The most preferred calcination temperature range is from 350° C. to 500° C.

The product obtained from this step is then treated with a solution containing a source of cobalt ions, in order to form the crystalline aluminosilicate of formula (I). This step takes place under similar conditions to the treatment with the source of M1 ions described above. Solutions of cobalt salts are convenient for this purpose. The solvents used to dissolve the salt(s) may be organic or inorganic, the only requirement being that the salt(s) be soluble in the particular solvent. Hydroxylic solvents are preferred, in particular water.

Organic solvents may be useful for metal salts which have organic ionic components such as carboxylates, sulphonates, alkoxides etc. The preferred solutions are aqueous solutions of readily water soluble salts, such as bicarbonates, carbonates, chlorated, perchlorates, hypochlorites, nitrates, nitrites, sulphates, hydrogen sulphates, sulphates, iodatates, halides, and the like.

Treatment with the solution containing the source of cobalt ions is performed under conditions that allow control of the amount of cobalt ions incorporated into the zeolite framework. This is necessary to adjust the catalytic properties of the crystalline aluminosilicate of formula (I). The cobalt ions will displace principally the M1 ions. Replacement of the M1 ions may be complete (z=0); partial replacement of the M1 ions is however preferred.

Any conventional impregnation method known to those skilled in the art may be used to perform the treating in step (d). For example, the zeolite can be dipped in a large volume of solution, which is in excess of the pore volume of the zeolite, removed and shaken of excess liquid. Alternatively, an amount of impregnating liquid considerably less than the pore volume can be sprayed onto an agitated bed of zeolite. Alternatively, the volume of impregnating liquid can range from about the pore volume to about four of five times, preferably about twice the pore volume of the zeolite to be impregnated. In yet another alternative, a dry impregnation technique can be used, in which just that amount of impregnating solution is used, which will just fill the pores of the zeolite. In other embodiments, baskets of zeolite are dipped into a vat of impregnating solution, removed and dried. Alternatively, the zeolite may be tumbled with the impregnating solution.

The process may also contain an additional step (e), in which the crystalline aluminosilicate obtained in step (d) is calcined. Preferably, a careful calcination method, in which the cobalt-exchanged aluminosilicate is first heated under nitrogen, to moderate temperature, such as less than 250° C., preferably no more than 200° C., followed by further heating with introduction of oxygen to a temperature of greater than 300° C. but no greater than 550° C., most preferably between 350° C. to 500° C. for several hours, before cooling down to room temperature under nitrogen.

The exchange with a solution containing the M1 ions takes place before the exchange with a solution containing cobalt in order to stabilize the structure during the ion exchange treatments. Without wishing to be bound by theory it is believed that incorporation of cobalt into crystalline aluminosilicates with high aluminium content such as faujasite causes stress and damage. Hydrolysis of the hexaquo complexes leads to de-alumination and eventual destruction of the crystalline aluminosilicate framework. Furthermore, cobalt is known to distort the six-rings of crystalline aluminosilicates by twisting the three outer oxygen atoms of the six-ring towards its centre, thereby introducing considerable strain. Besides framework destabilization, the strongly held hydration spheres of the cobalt ions impede complete exchange of crystalline aluminosilicate source material with cobalt because the large hexaquo complex cannot enter the small cavity system. Therefore stabilization of the crystalline aluminosilicate framework is necessary. The exchange of the crystalline aluminosilicate with the alkaline earth metal M1 leads to occupancy of the small cavity system by the alkaline earth metal. Theoretically, complete occupancy of all hexagonal prisms requires introduction of 16 alkaline earth metal ions per unit cell. After calcination the alkaline earth metal is confined in the hexagonal prisms. Therefore after secondary exchange with cobalt and calcination, the cobalt ions are forced into the supercages, where they are available for catalysis. Theoretically, to obtain a loading of 1 cobalt species per supercage, 8 cobalt ions have to be introduced per unit cell. Alkaline earth metal in the small cavity effectively stabilizes the tetrahedral framework.

In addition to the crystalline aluminosilicate, the catalyst composition may also include an inorganic oxide material matrix or binder. Such matrix materials include synthetic or naturally occurring substances as well as inorganic materials such as clay, alumina, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

Specific useful catalyst matrix or binder materials employed herein include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of the crystalline aluminosilicate and binder or matrix, if present, may vary widely with the crystalline material or crystalline aluminosilicate content ranging from about 1 to about 99 percent by weight, and more usually in the range of about 30 to about 80 percent by weight of the total catalyst.

Oligomerization

In the present invention the olefin feed is contacted with the oligomerization catalyst under conditions suitable for oligomerization.

The olefin oligomerization reaction system may include one or more of a fixed bed reactor, a packed bed reactor, a tubular reactor, a fluidized bed reactor, a slurry reactor, a continuous catalyst regeneration reactor, and any combination thereof. These reactors may be operated in any combination such as, for example, in series and/or parallel sequence. In several embodiments, they may be operated in semi-continuous (i.e. continuous but down for routine maintenance), continuous, or batch mode.

The oligomerization conditions may vary within broad limits, depending on the type of olefin feed used. Regarding temperature ranges, they should not be so high that deoligomerizaiton rates predominate over the oligomerization reaction, thereby preventing practical operation. Suitable temperature ranges typically include temperatures from 50° C. to 300° C., such as from 80° C. to 250° C., or even 100° C. to 200° C. Preferable ranges include from 105° C. to 150° C., and even more preferably from 115° C. to 130° C. Advantageously, the oligomerization process of the present invention can be operated at temperatures lower those typically used with zeolite catalysts.

The pressure employed during oligomerization may also vary within broad limits, depending on the type of olefin feed and temperature used. It is typically in the range of from 5 to 8 MPa and is preferably 6 to 7.5 MPa.

The feed weight hourly space velocity (WHSV) based on catalyst weight i.e. g of feed/g of catalyst, may be in the range of from 0.1 to 20 $hr^{-1}$ and preferably any of 0.5 to 4 $hr^{-1}$, 5 to 8 $hr^{-1}$ and 9 to 13 $hr^{-1}$.

In one embodiment, the process is conducted at a temperature of 50-300° C.; a feed weight hourly space velocity of 0.1 to 20 $hr^{-1}$; and a pressure of 5 to 8 MPa. In another embodiment, the process is conducted at a temperature of 105-150° C.; an olefin weight hourly space velocity of any of 0.5 to 4 $hr^{-1}$, 5 to 8 $hr^{-1}$ and 9 to 13 $hr^{-1}$; and a pressure of 6 to 7.5 Mpa.

The products of olefin oligomerization are usually mixtures of, for example, olefin dimers, trimers, and higher oligomers. Further, each olefin oligomer is itself usually a mixture of isomers, both skeletal and in double bond location. Highly branched isomers are less reactive than linear or lightly branched materials in many of the downstream reactions for which the oligomers are used as feedstocks. This is also true of isomers in which access to the double bond is sterically hindered. In this specification, the olefin types of the oligomers can be denominated according to the degree of substitution of the double bond, as follows:
Type I: R—CH=CH$_2$, mono-substituted
Type II: R—CH=CH—R, di-substituted
Type III: RRC=CH$_2$, di-substituted
Type IV: RRC=CHR, tri-substituted
Type V: RRC=CRR, tetra-substituted
wherein R represents an alkyl group, each R being the same or different. The olefin type may be identified by proton NMR analysis.

As discussed above, the degree of branching also affects the reactivity of the oligomer olefins. The branching index for an oligomer having n carbon atoms can be determined by gas chromatography, after hydrogenation of the olefinic oligomers, and by adding the areas under peaks corresponding to mono-, di- and tri-etc. branched isomers in the mixture, multiplied by their respective number of branches and dividing the sum by the total area under the peaks of all isomers having n carbon atoms. For example in an oligomer product mixture, where the C8 oligomeric portion consists of 10% linear C8, 30% mono-branched C8, 50% di-branched C8, 10% tri-branched C8, the C8 branching index (BI) is calculated as follows:

$$BI=[(0\times10)+(1\times30)+(2\times50)+(3\times10)]/100=1.6$$

Preferably, the oligomerization process of the invention predominantly produces olefin dimers. Preferably the olefin feed comprises butenes and the oligomer product comprises octenes. The branching index of the oligomer product may be less than 2.5, preferably less than 2 and even more preferably less than 1.25. It is most preferred when the branching index is between 1 and 1.25.

The oligomer (Higher Olefin) product is useful in many applications and is the starting material for further conversion processes. For example, the oligomer product may be polymerized to produce polyolefins that have application in the plastic industry or polymerized to form synthetic basestocks for lubricants. The oligomer product may undergo hydroformylation and subsequently hydrogenation to produce alcohols. The alcohols may be used in industry such as, for example, solvents, or be incorporated into the production of detergents/surfactants. Detergent products having low branching indexes and low levels of hindered olefins are particular useful as they have better hard water solubility and better biodegradability resulting from the lower levels of quaternary carbons. The alcohols may further be used in many other areas of industry such as, for example, undergoing esterification to produce esters that have application as plasticizers. The oligomer product may also be a blend component for fuels.

The invention will now be demonstrated with reference to the Figures by way of example only.

EXAMPLES

Example 1

Preparation of NaCaCo-Zeolite Y—Catalyst I

The catalyst was prepared by stirring 5 g of NaY zeolite (available from Zeocat), having a composition Na$_{52}$Al$_{52}$Si$_{140}$O$_{384}$ and Si/Al ratio of 2.69, and 635 ml of a 0.01 M aqueous solution of CaCl$_2$ for 12 hours in a round bottom flask using magnetic stirrers at room temperature. The zeolite was washed on a Buchner funnel with distilled water and dried at 60° C. followed by calcination under an oxygen flow with a ramping rate of 2° C./min to 500° C., and maintaining the sample for 8 hours at 500° C. A sample of this Ca-exchanged material was submitted to X-ray diffraction (XRD) analysis for a detailed analysis of its crystal structure and elemental analysis, and determined to have the composition Na$_{19.1}$Ca$_{16.5}$Al$_{52}$Si$_{140}$O$_{384}$.

XRD measurements were recorded on a STOE STADI MP diffractometer with focusing Ge(111) monochromator (CuKα$_1$ radiation) in Debye-Scherrer geometry with a linear position sensitive detector (PSD) (6° 2θ window) from 3 to 90.99° 2θ, with a step width of 0.5°, internal PSD resolution 0.01°, and a steptime of 300 seconds. Powder samples were sealed in capillaries of inner diameter 0.5 mm. Measurements occurred at room temperature. Rietveld Refinement was performed with the GSAS software package.

FIG. 1 shows the XRD pattern obtained for the calcined material, as well as a structure model for the crystal unit cell, derived from the detailed XRD analysis.

3 g of the calcined NaCaY sample prepared above and 300 ml of a 0.01M CoCl$_2$ solution were placed in a round bottom flask and stirred using magnetic stirrers for 6 hours at room temperature. The sample was washed on a Buchner funnel with distilled water and dried at 60° C. The dried sample was then calcined under the following conditions: 4 hours of nitrogen flow at 200° C., followed by 4 hours of oxygen flow at 450° C., followed by cooling down to reaction temperature under nitrogen flow. A sample of this Co-exchanged material was submitted to X-ray analysis for a detailed analysis of its crystal structure and elemental analysis, and determined to have the composition Na$_{9.1}$Ca$_{12.2}$CO$_{9.2}$Al$_{52}$Si$_{140}$O$_{384}$.

Figure 2:
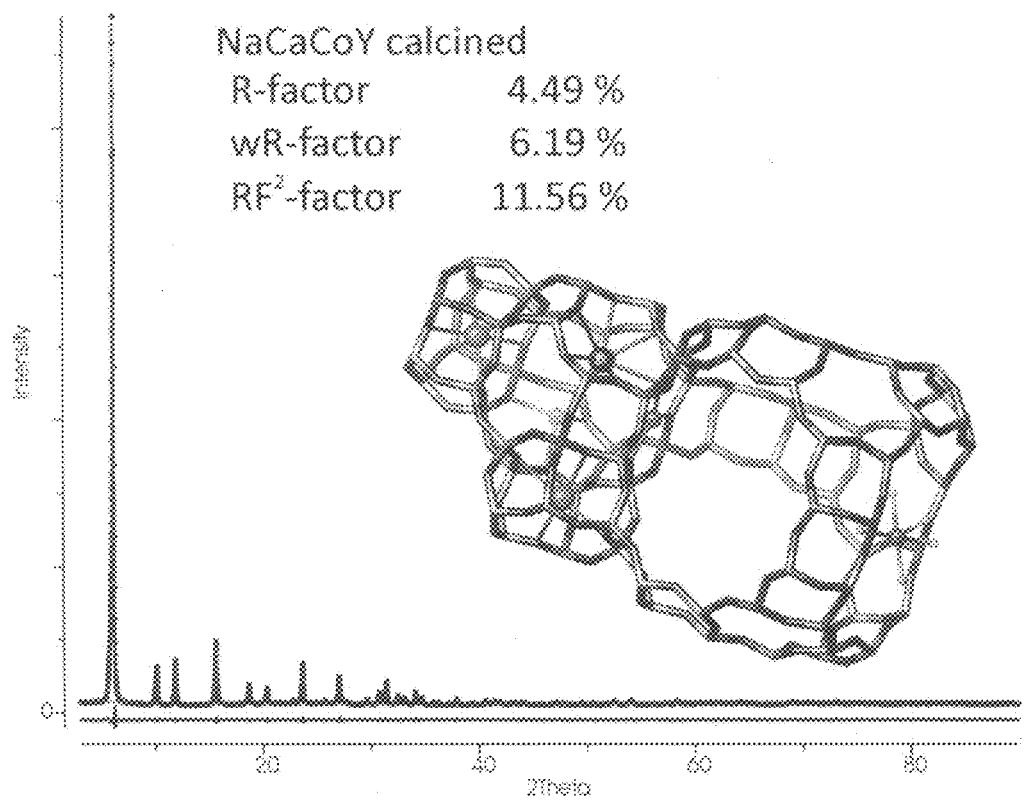
FIG. 2: XRD pattern of calcined NaCaCoY prepared in example 1.

FIG. 2 shows the XRD pattern obtained for this calcined material, as well as a structure model for the crystal unit cell, derived from the detailed XRD analysis.

Example 2

Butene Oligomerization Using Catalyst I

Catalyst I prepared at example 1 was tested in a butene oligomerization process, using a feed consisting of 90.2 wt % n-hexane, 8.5 wt % i-butane and 1.3 wt % 1-butene.

The reactor used in these tests was a fixed-bed continuous flow reactor, equipped with a stainless steel 316 reactor tube. The catalyst was tested at six different reaction temperatures. The catalytic experiments were performed in a fixed bed down flow reactor. The catalysts were crushed into pellets with diameters of 250-500 µm. The dead volume of the reactor was filled with glass beads of similar diameters. Product samples were taken with a sampling valve with internal volume of 0.1 µL and analyzed by on-line gas chromatography.

The online gas chromatograph (GC) used was a Hewlett Packard 5890 series, equipped with a 60 m×0.53 mm column with a chemically bonded poly-dimethyl-siloxane (CP-SIL-5CB) film as stationary phase with an initial thickness of 5 µm.

The olefin feed was pressurized and delivered to the reactor by means of an electronic liquid mass controller. The reactor pressure was kept constant at 7 MPa. Reaction temperatures were varied over 6 runs between 100 and 130° C. as can be seen in Table 2. Space velocities are given in Table 1 for each run at its specific reaction temperature. Weight hourly speed velocity (WHSV) is expressed as $g_{feed}$/hour divided by the catalyst weight.

Figure 3:
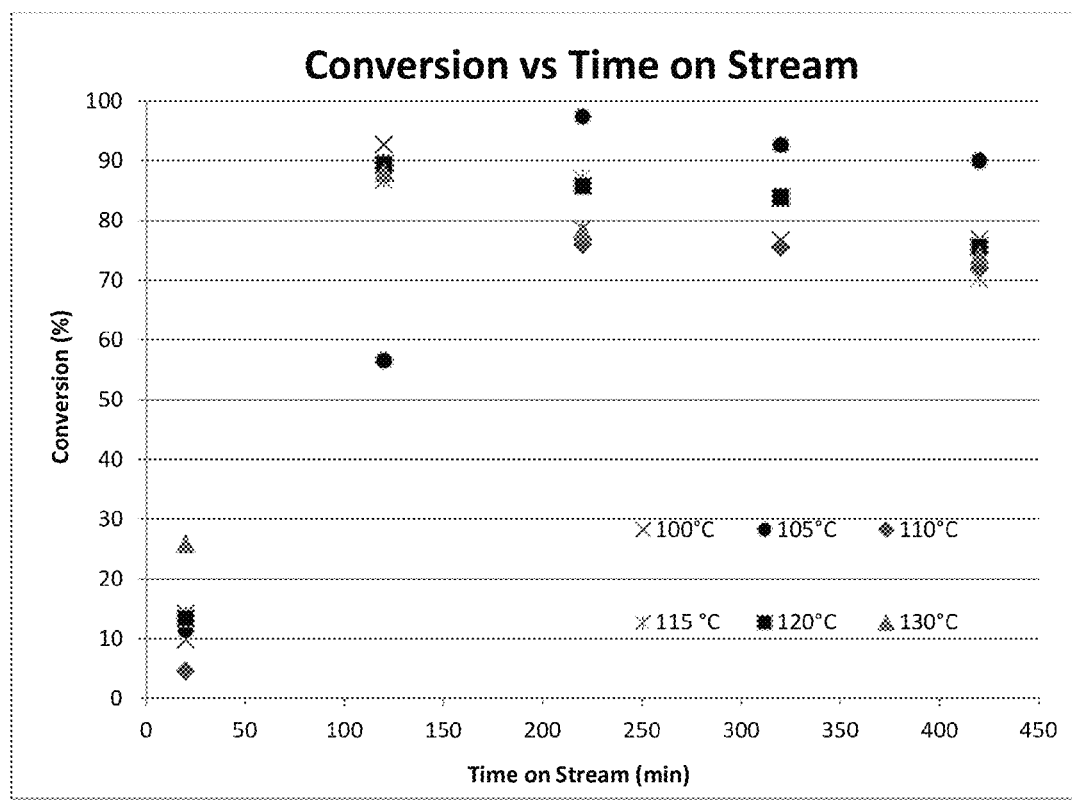
FIG. 3: shows the butene conversion versus time on stream for the tests described in Example 2.
Figure 4:
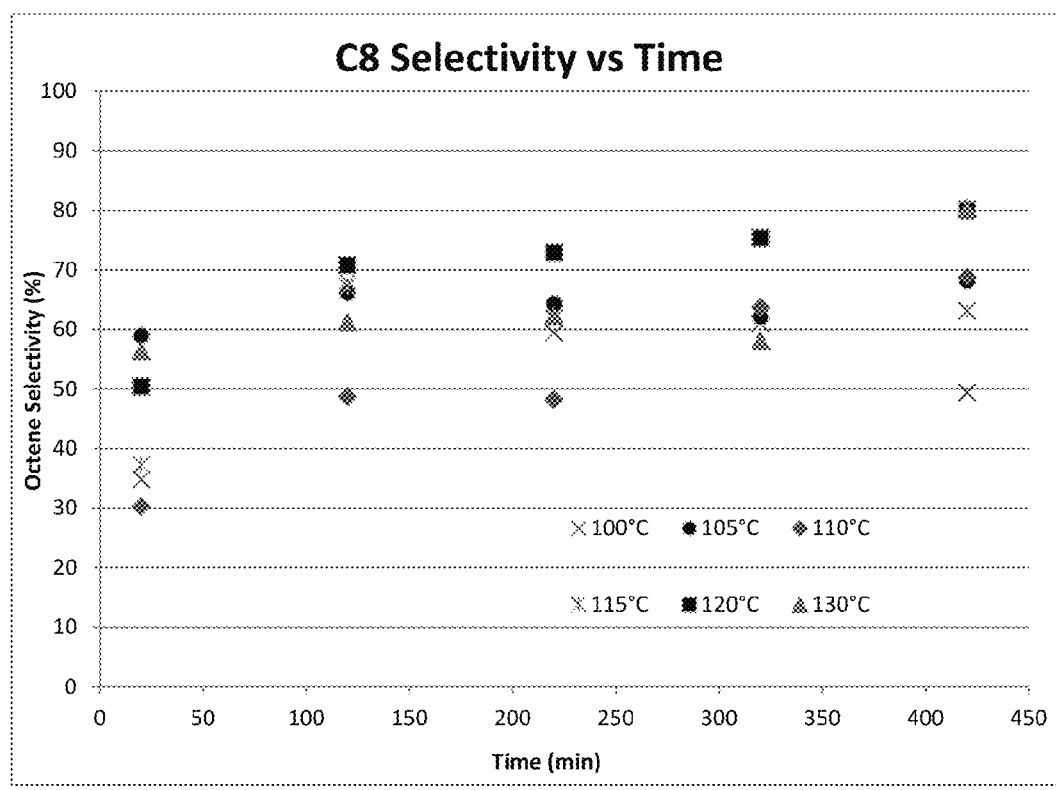
FIG. 4: shows the octene product selectivity versus butene conversion for the tests described in Example 2.
Figure 5:
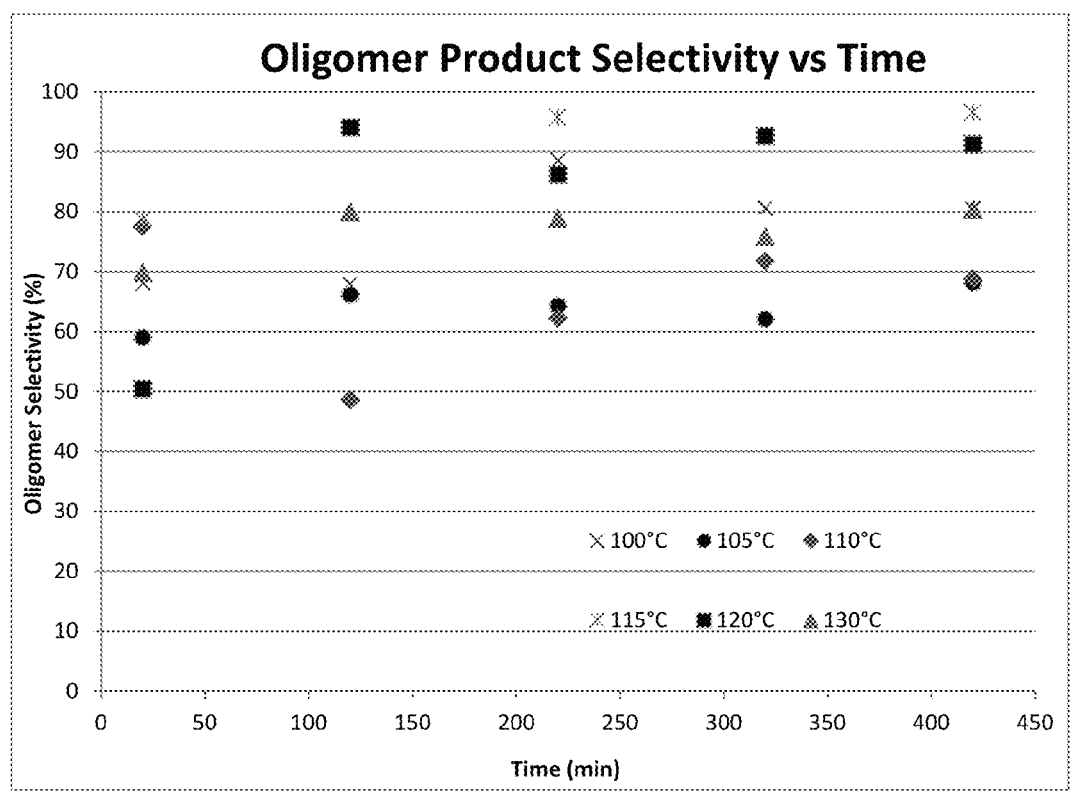
FIG. 5: shows the total oligomer product selectivity versus butene conversion for the tests described in Example 2.

Plots of butene conversion to octenes versus time on stream are given in FIG. 3. It can be seen that at a temperature of 105° C. the highest conversions are obtained, ending at 90% converted butene at the end of the reaction cycle. For other temperatures the global trend is similar, reaching conversions around 75%. FIG. 4 shows the octene product selectivity versus butene conversion. FIG. 5 gives the total oligomer product selectivity versus butene conversion. The total oligomer selectivity is calculated as the sum of the C8, C12 and C16 oligomer products. The rest of the products are descending from cracking reactions.

TABLE 1

| Temperature (° C.) | Catalyst Wt (g) | WHSV feed (g/g · hr) |
|---|---|---|
| 130 | 1.5012 | 9.53 |
| 120 | 1.5017 | 9.52 |
| 115 | 2.0048 | 7.13 |
| 110 | 1.505  | 9.50 |
| 105 | 2.0207 | 7.08 |
| 100 | 2.0013 | 7.15 |

Despite higher conversion at 105° C., temperatures between 120° C. and 130° C. yielded higher octene selectivities at around 80%. The most stable performance and the smallest amounts of cracking products were detected between 120° C. and 115° C. Therefore the range between 115° C. and 130° C. was identified as optimum operation temperatures. This is the first time a heterogeneous cobalt based catalyst has shown such good activity in oligomerization of 1-butene.

Two samples were taken for offline GC analysis to determine the branching degree of the octene isomers. The samples were taken at the end of the reaction at 130° C. and 120° C., after 400 minutes on stream. The results showing the % isomer product distribution for the two samples analyzed in this fashion can be found in Table 2.

TABLE 2

| Temp (° C.) | n-octene | 3MC7 (a) | 2,4 + 2,5 DMC6 (b) | 3,4 DMC6 (c) | 2,2 DMC6 (d) | B.I. (e) |
|---|---|---|---|---|---|---|
| 130 | 30.2 | 29.3 | 19.9 | 6.9 | 13.7 | 1.10 |
| 120 | 24.2 | 29.5 | 20.5 | 8.6 | 17.3 | 1.22 |

(a) 3-methylheptane; (b) 2,4 and 2,5 dimethylhexane; (c) 3,4 dimethylhexane; (d) 2,2 dimethylhexane (e) Branching Index It can be seen that high conversion, high octene selectivity and remarkably low branching degrees in the oligomer product, even as low as around 1.1, are achieved using the cobalt loaded zeolite catalyst of the present invention.

Example 3

Preparation of NaBaCo-Zeolite Y—Catalyst II

The catalyst was prepared by stirring 5 g of NaY (available from Zeocat) having a composition $Na_{52}Al_{52}Si_{140}O_{384}$ and Si/Al ratio of 2.69, with 1 liter of 0.05M $BaCl_2$ for about 12 hours at room temperature in a round bottom flask using magnetic stirrers. The resulting powder was washed on a Buchner funnel with distilled water and dried at 60° C. followed by calcination at 500° C. under dry air for about 6 hours. A sample of this Ba-exchanged material was submitted to inductively coupled plasma atomic emission spectroscopy (ICP-AES) using the Optima 5300 DV (Perkin Elmer) instrument for elemental analysis. The exchanged material was determined to have the composition $Na_{17.3}Ba_{17.3}Al_{52}Si_{140}O_{384}$. 10 g of the Ba(Na)Y zeolite was then stirred with 537 ml of a 0.01 $CoCl_2$ solution for about 6 hours at room temperature in a round bottom flask using magnetic stirrers. The sample was then washed on a Buchner with distilled water and dried at 60° C., followed by careful calcination by heating under nitrogen flow at 200° C., followed by 2 hours under oxygen at 450° C.

Example 4

Butene Oligomerization Using Catalyst II

The NaBaCoY catalyst prepared in example 3 was tested in a butene oligomerization process, using a feed consisting of 1.3 wt % 2-butene in n-hexane. The tests were performed in the same reactor system as Example 2 at a pressure of 70 barg at a total feed rate of 23.8 g/h (=0.309 g/h butene-2 feed rate).

At the start up temperature of 100° C. already 80% conversion was obtained. At 140° C. a constant conversion of 90% was obtained without any apparent deactivation up to 600 min time on stream. The run was deliberately stopped at this point in time. Product analysis was the same as carried out in Example 2.

A C8 selectivity of 70 wt %, 15 wt % to C12 and 9 wt % to C16 was achieved.

The remainder consisted of cracked products i.e. oligomers in the C9-C11 range. The C8 oligomer product had the following isomer composition which leads to an average branching of 2.01:
Linear 0.4 wt %
Mono-branched: 2.1 wt %
Di-branched: 93.9 wt %
Tri-branched: 3.7 wt %

It can be seen that high conversion, high octene selectivity and low triple branching in the oligomer product, starting from a relatively less reactive olefin such as 2-butene and at a relatively low start up temperature, are achieved using the cobalt loaded zeolite catalyst of the present invention.

The invention claimed is:

1. An olefin oligomerization process comprising contacting an olefin feed with a catalyst composition under conditions suitable for oligomerization, wherein the catalyst composition comprises a crystalline aluminosilicate having the FAU, the EMT or a combination of FAU and EMT framework types, said crystalline aluminosilicate having cobalt and at least one alkaline earth metal selected from calcium, barium, strontium and mixtures thereof within its intracrystalline cages.

2. The olefin oligomerization process of claim 1, wherein the crystalline aluminosilicate has a composition according to formula (I):

$$Co_xM1_yM2_zAl_pSi_{192-p}O_{384} \quad (I)$$ 

in which:
p is the number of aluminium atoms per mol of aluminosilicate, and p is at least 40, but is not greater than 96;
x is the number of Co atoms per mol of aluminosilicate and x is at least 4, but is not greater than (p/2)−5;
M1 is calcium, barium, strontium or a mixture thereof;
y is the number of M1 atoms per mol of aluminosilicate, and y is at least 5, but is not greater than (p/2)−x;
M2 is sodium, potassium or a mixture thereof;
z is number of M2 atoms per mol of aluminosilicate, and z≥0 with z=p−2x−2y.

3. The olefin oligomerization process of claim 2, wherein p is at least 50, but is not greater than 76, x is at least 4 and is not greater than 10, y is at least 10 and is not greater than 16 and z>0 and z=p−2x−2y.

4. The olefin oligomerization process of claim 2, wherein M1 is calcium.

5. The olefin oligomerization process of claim 2, wherein M2 is sodium.

6. The olefin oligomerization process of claim 1, wherein the crystalline aluminosilicate has the FAU framework type.

7. The olefin oligomerization process of claim 6, wherein the crystalline aluminosilicate is zeolite Y.

8. The olefin oligomerization process of claim 2, wherein the olefin feed comprises C3 to C6 olefins.

9. The olefin oligomerization process of claim 8, wherein the olefin feed comprises butene.

10. A crystalline aluminosilicate of the FAU, the EMT or a combination of the FAU and EMT framework types, having a composition according to formula (I):

$$Co_xM1_yM2_zAl_pSi_{192-p}O_{384} \qquad (I)$$

wherein:
p is the number of aluminium atoms per mol of aluminosilicate, and p is at least 50, but is not greater than 76;
x is the number of Co atoms per mol of aluminosilicate and x is at least 4 and is not greater than 10;
M1 is calcium, barium, strontium or a mixture thereof;
y is the number of M1 atoms per mol of aluminosilicate, and y is at least 10, but is not greater than 16;
M2 is sodium, potassium or a mixture thereof;
z is the number of M2 atoms per mol of aluminosilicate, and z>0 with z=p−2x−2y.

11. The crystalline aluminosilicate of claim 10, wherein M1 is calcium.

12. The crystalline aluminosilicate of claim 11, wherein M2 is sodium.

13. The crystalline aluminosilicate of claim 10, wherein the crystalline aluminosilicate has the FAU framework type.

14. The crystalline aluminosilicate of claim 13, wherein the crystalline aluminosilicate is zeolite Y.

* * * * *